United States Patent [19]

Bohn

[11] Patent Number: 5,592,952

[45] Date of Patent: Jan. 14, 1997

[54] INFECTION CONTROL SURGICAL DRAPE AND METHOD OF MAKING SURGICAL INCISION

[76] Inventor: William W. Bohn, 6720 Willow La., Mission Hills, Kans. 66208

[21] Appl. No.: 516,797

[22] Filed: Aug. 18, 1995

[51] Int. Cl.⁶ ................................................. A61B 19/00
[52] U.S. Cl. .......................................... 128/849; 128/853
[58] Field of Search .................................... 128/849–856

[56] References Cited

U.S. PATENT DOCUMENTS

| | | | |
|---|---|---|---|
| 4,040,418 | 8/1977 | Collins . | |
| 4,323,062 | 4/1982 | Canty | 128/852 |
| 4,334,529 | 6/1982 | Wirth | 128/852 |
| 4,524,767 | 6/1985 | Glassman . | |
| 4,574,796 | 3/1986 | Lundström et al. . | |
| 4,607,631 | 8/1986 | Hanssen . | |
| 4,664,103 | 5/1987 | Martin | 128/852 |
| 4,711,236 | 12/1987 | Glassman . | |
| 4,889,136 | 12/1989 | Hanssen . | |
| 5,038,798 | 8/1991 | Dowdy | 128/849 |
| 5,383,476 | 1/1995 | Peimer et al. . | |

OTHER PUBLICATIONS

Information and Specification Sheet for OrthoArts Hip Sheet, Kimberly–Clark Corporation, Publication No. KL–878.

Information and Specification Sheet for MB&J Hip Drape featuring INSIGHT™ Clear Viewing Panel Product No. 3568, Microtek Medical, Inc., Lit. No. 0246.

Primary Examiner—Michael A. Brown
Attorney, Agent, or Firm—Hovey, Williams, Timmons & Collins

[57] ABSTRACT

A surgical drape is provided for reducing the potential for contamination at a surgical incision site which includes a first sheet having an opening for passing a body part therethrough and a second sheet connected to the first sheet proximate the opening. The second sheet is preferably of transparent synthetic resing material having adhesive coating on one side thereof. A third sheet may be provided, with the body part positioned between the second and third sheets. The second and third sheets may be connected along their respective side edges to isolate the surgical incision area. In the corresponding method, an incision may be made through the transparent second sheet, with the second sheet adhering to the body part to limit the contamination of the incision site by solids or fluids contacting or coming from the surrounding tissue.

25 Claims, 3 Drawing Sheets

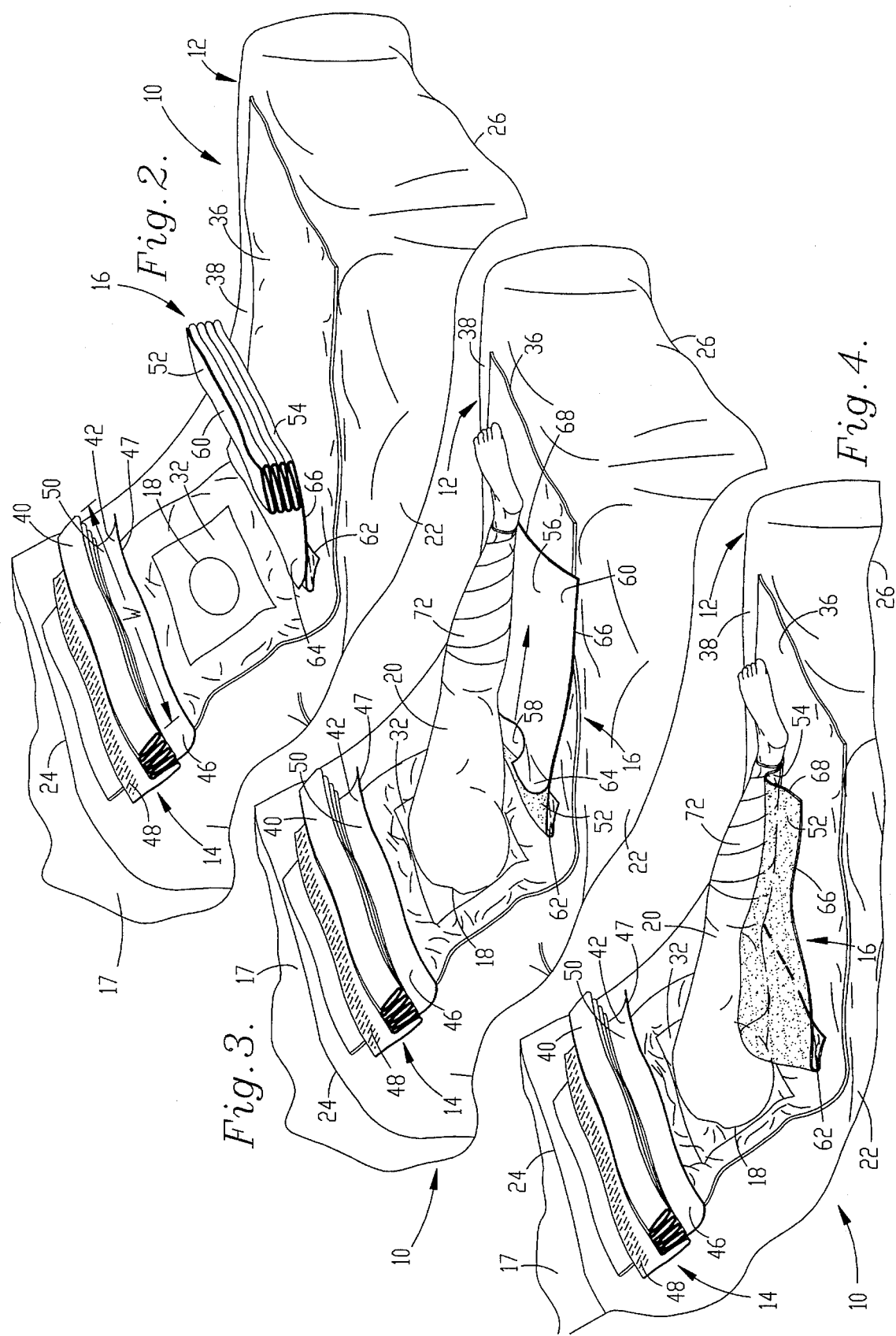

INFECTION CONTROL SURGICAL DRAPE AND METHOD OF MAKING SURGICAL INCISION

BACKGROUND OF THE INVENTION

1. Field of the Invention

This invention broadly concerns a surgical drape for reducing contamination at an incision site during surgery. More particularly, it is concerned with a surgical drape and method for making a surgical incision which provides for covering the incision site with a sheet and adhering the sheet in covering relationship to the incision site.

2. Description of the Prior Art

One principal concern of all surgeons is the need for maximum cleanliness and sterilization in the operating area. Since the discoveries of Joseph Lister, increasing attention has been devoted to the ensuring that, to the maximum extent possible, surgical instruments and operating room equipment and personnel are sterile. To this end, surgical personnel wear sterile gowns and gloves, use masks to avoid contamination of the surgical site, and wash thoroughly prior to surgery. These precautions extend to both human and veterinary surgery.

In addition to these efforts, surgical personnel attempt to isolate the incision site from contamination from the patient. The human or animal patient typically receives an application of a topical antiseptic scrub at the incision site in order to kill organisms which might enter the open wound. In addition, clean linens and drapes are used to cover the surrounding body tissue to limit contamination at the wound site.

More recently, surgical drapes have been developed which provide added features. A hip drape developed by the Missouri Bone and Joint Clinic in Saint Louis, Mo. has been offerred by Microtek Medical, Inc. which includes a clear viewing panel creating an anesthesia screen permitting visual communication between the anesthesiologist and the surgical team. Another surgical drape is shown in U.S. Pat. No. 4,711,236 to Glassman which includes a base drape including an opening for receiving a human limb therethrough and a detachable incise drape for wrapping around and enclosing the operable portion of the limb.

These drapes have distinct advantages over conventional linen sheets, but may be difficult to handle. For example, the Glassman drape requires separation of the incise drape and wrapping around the incision. It is desirable to avoid the need to separate a sheet and wrap the same around a limb, especially for broken limbs, and in any event to limit contact with the patent's skin. Moreover, wrinkles and the like are inevitable in attempting to wrap a sheet of material in adhesion to conform to an irregular surface such as a limb.

Accordingly, there has developed a need for a surgical drape which presents enhanced ease of application and isolation to a surgical site.

SUMMARY OF THE INVENTION

This and other objects of the present invention are provided in accordance with the surgical drape and the method of making a surgical incision in accordance with the present invention. The surgical drape hereof is uniquely configured to isolate a sugical incision against contamination by continuous and uninterrupted extension from the opening through which the limb passes to an area below the incision site.

The invention broadly includes a base sheet defining an opening therein for receiving a body part, such as a limb, therethrough, and at least one incise sheet attached to the base sheet adjacent the opening and extendable therefrom to adhesively attach to the patient. A second incise sheet may be provided in opposition to the first incise sheet whereby the body part surrounding the incision may be completely enclosed and the limb adjacent the opening thereby encased in by the incise sheet. The surgical drape hereof permits the surgeon to make an incision through the clear incise sheet or sheets, while substantially inhibiting the introduction of body fluid, tissue or other debris into the wound.

In preferred embodiments, the incise sheets are initially presented in a folded or corrugated configuration, whereby the incise sheets remain compact and out of the surgeon's way until extended for application to the patient. Each incise sheet is preferably provided with a release carrier covering the adhesive coating on one side of the incise sheet. The release carrier includes a free flap located adjacent the area of attachment between the incise sheet and the base sheet. The release carrier is pulled from the incise sheet as the latter is extended over the body part for ease of application, largely avoiding the premature contact of the adhesive on the incise sheet with undesired objects or even potential contaminants.

In particularly preferred embodiments, the base sheet is provided with an elastomeric panel surrounding the opening. A thin foam web may be provided around the opening to provide a reception site for hook and loop fabric attachments and to provide absorption for body fluids emanating from the incision. A clear anesthesiologist screen may be attached at one end of the base sheet to provide a barrier to further introduction of contaminants and to permit the anesthesiologist to observe and communicate visually with the surgical team during the operation.

The invention hereof also contemplates a companion method of protecting an incision site against contamination during surgery, including the steps of providing a base sheet having an opening therein and an incise sheet attached to the sheet adjacent the opening, extending the incise sheet while one end remains attached to the base sheet, with the incise sheet extended over the incision site and adhered to the body part in surrounding relationship to the incision site, and then making a surgical incision at the incision site through the incision sheet.

These and other features of the present invention will be readily appreciated by those skilled in the art with reference to the drawing and detailed description set forth below.

BRIEF DESCRIPTION OF THE DRAWINGS

FIG. 2 is an isometric view similar to FIG. 1 showing the drape ready for receipt of the patient and omitting the anesthesiologist screen;

FIG. 3 is an isometric view similar to FIG. 2 showing the patient's leg passing through the opening in the first sheet of the drape with the lower incise sheet extended while connected to the first sheet;

FIG. 4 is an isometric view similar to FIG. 3 showing the removal of the release carrier on the lower incise sheet which has been adhered to the patient's leg;

DESCRIPTION OF THE PREFERRED EMBODIMENT

Figure 1:
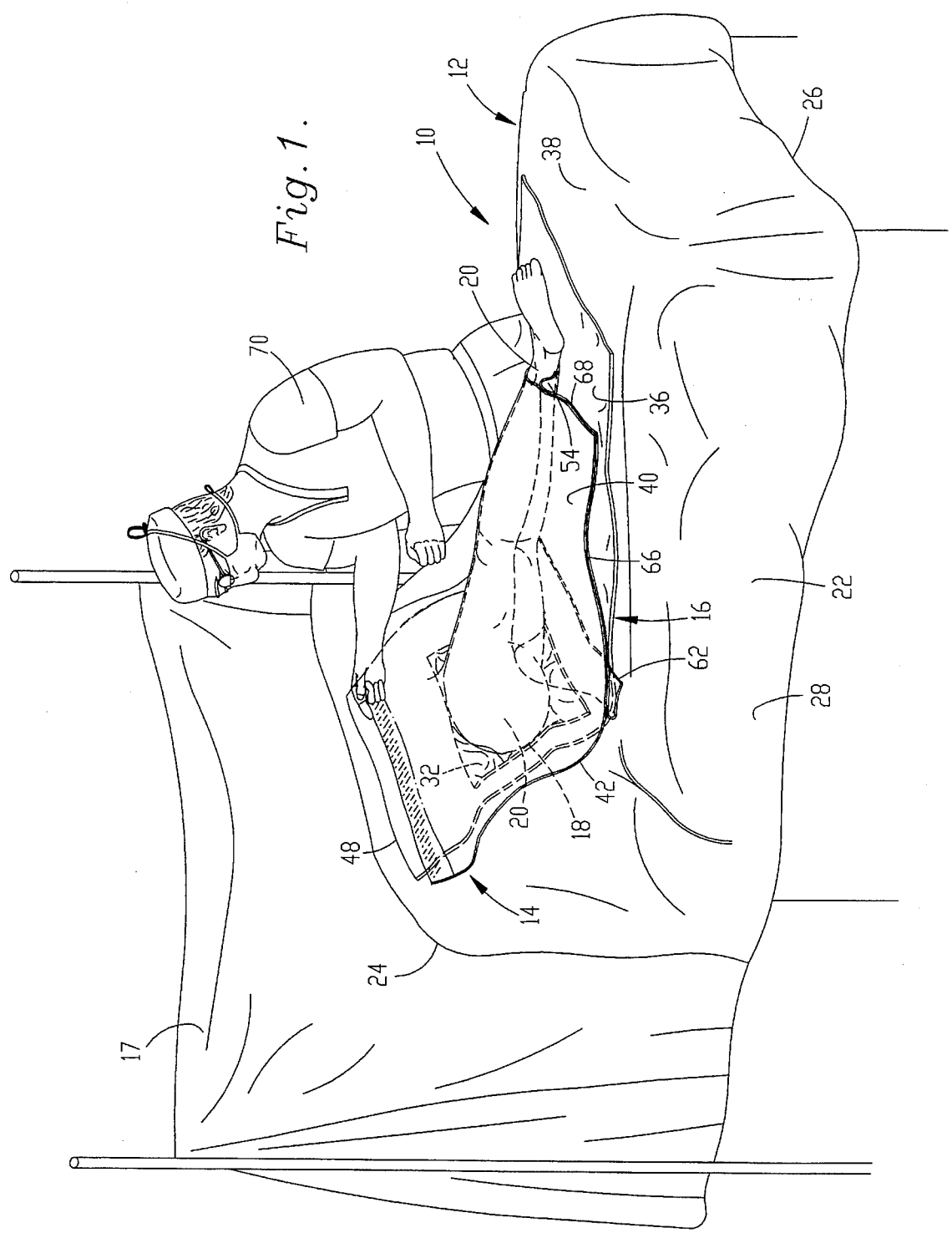
FIG. 1 is an isometric view of the surgical drape of the present invention, showing the clear anesthesiologist screen but omitting the head and torso of the patient.

Referring now to the drawing, a surgical drape 10 in accordance the the preferred embodiment as shown in FIG. 1 broadly includes a base sheet 12, a first incise sheet 14 attached to the base sheet 12, a second incise sheet 16 attached to the base sheet 12, and an anesthesiologist screen 17 attached to the base sheet. The base sheet 12 includes an opening 18 defined therein for receiving a body part, such as a leg 20 of a patient therethrough.

In greater detail, the base sheet 12 includes a web 22 preferably made of paper in order to be economically disposable, but may be made of linen, cotton or other fabrics for greater durability. The base sheet 12 is preferably two sided an presents a proximate edge 24 and a remote edge 26, as well as a pair of side edges 28. The web 22 includes a cutout 30 (see FIG. 6) centrally positioned between the side edges 28 covered by an elastomeric panel 32. The elastomeric panel 32, made of latex or other suitable material, surrounds and defines opening 18, which is preferably circular in configuration and sized according to the body part to be inserted therethrough. Thus, the inital size of the opening for an adult leg would be greater than that of an infant, and an opening configured for receiving a leg sized greater than an arm. The size of the opening for receiving an adult leg would typically be about 5 inches, with the dimensions of the panel 32 preferably being about three times that size to provide adequate expansion to accomodate the body part therethrough. The panel 32 is positioned with its surrounding margin 34 intermediate a pad 36 and the front side 38 of the web 22, with the panel 32 adhesively attached to both the web 22 surrounding the cutout 30 and the underside of pad 36 (see FIG. 6).

The thin pad 36 of open-celled synthetic resin foam is adhesively attached to the normally uppermost front side 38 of the web 22. The pad 36 is of sufficient width and length to receive incise area of the leg 20 or other body part thereon, and preferably extends outwardly from the cutout 30 in order to provide sufficient absorbancy, and to serve, when desired, as a receptor site for hook and loop fabric attachments. The pad 36 is sufficiently thin so as to not inhibit folding of the base sheet 12 for packaging and storage.

The anesthesiologist screen 17 is adhesively attached along the proximate end 24 of the base drape. The screen 17 is preferably of transparent synthetic resin film extending along the transverse width of the base sheet 12 between the side edges 28.

Figure 5:
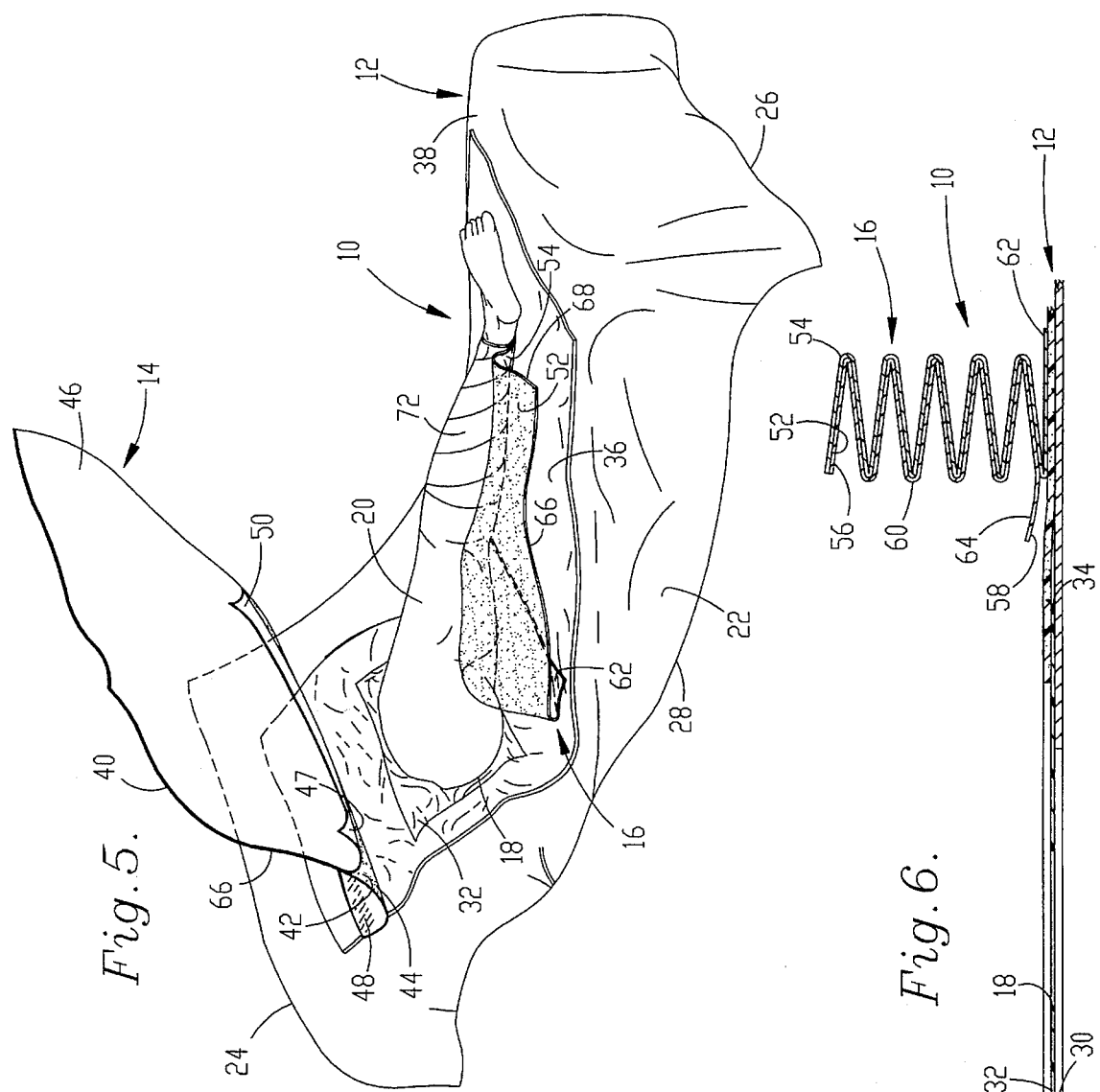
FIG. 5 is an isometric view similar to FIG. 4, showing the upper incise sheet extended while connected to the first sheet.

The first incise sheet 14 is preferably formed of transparent synthetic resin film and has an upper surface 40 and a lower surface 42 which is provided with a pressure-sensitive adhesive coating 44 (FIG. 5). A first release carrier 46 of synthetic resin or paper having a silicon release coating applied on a face 47 thereof is removably secured to the lower surface 42 of the incise sheet 14 to facilitate removal of the carrier 46 from the incise sheet when desired. The first incise sheet 14 is adhesively attached to the base sheet 12 along a proximate margin 48 of the first incise sheet 14, and positioned at the proximate side of the opening 18. The first release carrier 46 has a free flap 50 adjacent the proximate margin 48 of the first incise sheet 14, while the remainder of the release carrier 46 is adhered to the surface 42 of first incise sheet 14. The lower surface 42 faces the opening 18 when the first incise sheet is extended substantially perpendicular to the base sheet 12.

Figure 6:
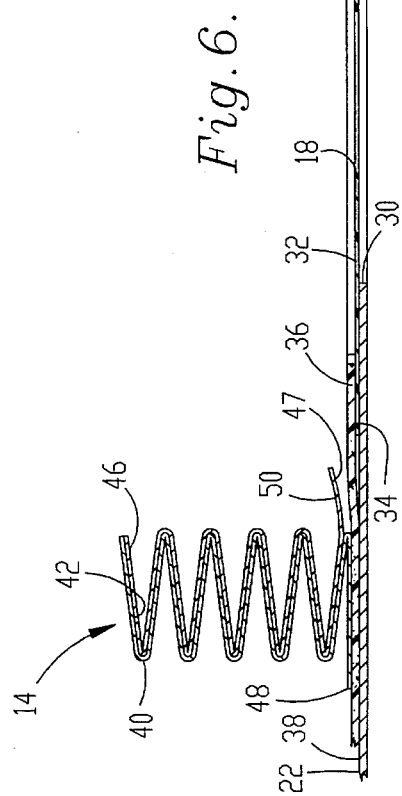
FIG. 6 is a vertical cross-sectional view taken through the thickness of the base sheet showing the pad and panel on the base sheet surrounding the opening.

The second incise sheet 16 is similar to the first incise sheet 14 in that it includes an adhesive-coated surface 52 and an uncoated surface 54 and is made of transparent synthetic resin film. A release carrier 56 having one side 58 provided with a silicon release coating and a second release coating-free side 60 is affixed to sheet 16. The one side 58 is attached to the adhesive coated surface 52 with the second side facing relationship to the opening as shown in FIG. 6. The second incise sheet 16 has a proximate edge 62 adhesively attached to the base sheet 12 opposite the opening 18 from the proximate margin 48 of the first incise sheet 14, with the proximate margin 48 and the proximate edge 62 oriented substantially parallel to one another. The release carrier 56 presents a free flap 64 extending toward the opening 18 prior to removal from the second incise sheet 16. The coated surface 52 faces upwardly when the second incise sheet is extended perpendicular to the base sheet 12.

The first incise sheet 14 and the second incise sheet 16 are stored in a fan-folded or rolled condition until ready for use. The first and second incise sheets preferably have the same transverse width W, which is sufficient to wrap around the leg 20 or other body part and join along common side edges 66. The first incise sheet 14, being located normally on the proximal side of the opening 18, may have a greater length than the second incise sheet 16 so that both incise sheets may be joined along a common end edge 68 (FIG. 1) after wrapping around the leg 20 or other body part.

In use, the surgeon 70 positions the body part of the patient through the opening 18, such that the incision will be made into the portion of the body part positioned over the pad 36. As illustrated in FIG. 1, a leg 20 extends through the opening 18 prior to knee surgery, so that the patient's knee is resting on the pad 36. The anesthesiologist screen 17 is extended upwardly to enhance the sterility of the incision site by providing a barrier against intrusion, while permitting visual as well as verbal communication between the surgeon and the anesthesiologist. A stocking or leg wrap 72 may be worn by the patient remotely from the opening 18. The elastomeric panel 32 conforms around the leg 20 so that the opening 18 conforms to the shape and size of the leg 20 or other body part engaged by the panel 32. The panel thus acts as a barrier to intrusion into the incision site by undesired contaminants behind and proximal to the opening 18.

With the leg 20 initially positioned as shown in FIG. 3, the surgeon or nurse then extends second incise sheet 16 by grasping the free flap 64 and pulling in a proximate to remote direction. As the release carrier 56 is peeled from the second incise sheet, the adhesive-coated surface 52 is applied to the leg 20 while the proximate edge 62 remains adhered to the base sheet 12. The release carrier 56 is peeled away until the second incise sheet 16 is fully extended and the adhesive-coated surface 52 is adhered to the leg 20 as shown in FIG. 4.

After the second incise sheet 16 has been extended and applied, the first incise sheet 14 is extended over the leg 20 as shown in FIG. 5. The surgeon or nurse grasps the free flap 50 and peels away the release carrier 46 from first incise sheet 14 which is applied on the opposite side of the patient's leg from the second incise sheet 16. As the lower surface 42 adheres to the leg, the first incise sheet 14 and the second incise sheet 16 join together along common side edges 66 to form a seal enveloping the patient's leg 20 substantially from the opening 18 along the length of the incise sheets. After the leg 20 has been enveloped by the clear incise sheets 14 and 16, the surgeon can make his incision through the incise sheet 14 (or both incise sheets as appropriate), with the adherence of the incise sheets to the skin inhibiting the introduction of biologoical contaminants into the wound.

Once the surgery is complete, the incise sheets 14 and 16 are peeled or cut away and the patient's body part is withdrawn through the opening 18 and the surgical drape 10 is disposed as appropriate.

Other advantageous aspects of the present invention may be appreciated. For example, a compact foldable drape 10 may be stored in a sterile package until just before use. The corrugated or rolled storage positions of the incise drapes limit exposure to contaminants until extended and applied to the patient. It may be further appreciated that the drape 10 hereof is not limited to human patients, but may be extremely helpful in treating expensive animals such as horses or breeding livestock, where disinfecting the area surrounding the incision is particularly difficult. Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as pertains to any apparatus not materially departing from but outside the liberal scope of the invention as set out in the following claims.

I claim:

1. A surgical drape for isolating a surgical site comprising, in combination:

a first sheet defining therein an opening adapted for receiving therethrough a body part;

a second sheet formed of transparent synthetic resin film and presenting a first side, a second side, a proximate margin, a remote margin, and a pair of opposite edges;

means connecting said proximate margin of said second sheet to said first sheet adjacent said opening in an orientation enabling said second sheet to be extended in covering relationship to said opening; and an adhesive coating on said first side of said second sheet for securing said second sheet to the body part during surgery.

2. A surgical drape as set forth in claim 1, including a third sheet presenting one side, another side, a near margin and a free margin, a pair of opposite edges, and means securing said near margin to said first sheet adjacent said opening and opposite said second sheet.

3. A surgical drape as set forth in claim 2, wherein said third sheet includes an adhesive coating on said one side, said one side positioned in facing relationship to said first side of said second sheet, said second sheet and said third sheet each presenting a respective width extending between their respective edges sufficient to cover said opening and sealingly interconnect adjacent their respective edges.

4. A surgical drape as set forth in claim 3, wherein said third sheet is provided of transparent synthetic resin film.

5. A surgical drape as set forth in claim 3, including a release liner releasably adhered to said one side of said third sheet.

6. A surgical drape as set forth in claim 5, wherein said third sheet presents a corrugated cross-sectional profile prior to removal of said release liner.

7. A surgical drape as set forth in claim 2, including a fourth sheet connected to said first sheet remotely from said opening, said fourth sheet being transparent on at least a portion thereof.

8. A surgical drape as set forth in claim 1, including a release liner releasably adhered to said first side of said second sheet.

9. A surgical drape as set forth in claim 8, wherein said second sheet presents a corrugated cross-sectional profile prior to removal of said release liner.

10. A surgical drape as set forth in claim 1, wherein said first sheet includes a panel of elastomeric material substantially surrounding said opening.

11. A method of making a surgical incision at an incision site on a body part during surgery comprising the steps of:

providing a surgical drape including a first sheet having an opening therein and a second sheet having a first side, a second side, a pair of side edges, a proximal margin and a remote margin, said second sheet being connected to said first sheet adjacent said proximal margin and adjacent said opening;

passing the body part of a patient through said opening to position the incision site over said first sheet;

extending the second sheet while connected to said first sheet over the opening;

adhesively affixing said second sheet to the body part in covering relationship to the incision site; and making an incision through the second sheet and into the body part.

12. A method according to claim 11, wherein said surgical drape includes a third sheet having a pair of side edges, one side and another side and connected to said first sheet opposite said second sheet, including the step of extending said third sheet opposite said second sheet with the body part therebetween.

13. A method according to claim 12, including the step of adhesively connecting said second sheet to said third sheet along portions of their respective side edges in sealing relationship.

14. A method according to claim 13, wherein said second and third sheets each present a transverse width sufficient to sealingly interconnect with one another along their respective side edges while enveloping the body part therebetween.

15. A method according to claim 12, including the step of adhesively connecting said third sheet to the body part opposite the second sheet.

16. A method according to claim 11, wherein the first sheet includes an elastomeric panel substantially surrounding said opening, including the step of positioning the body part to cause the elastomeric panel to stretch in engagement with the body part.

17. A surgical drape comprising:

a first base sheet including an elastomeric panel defining therewithin an opening configured to receive therethrough a body part;

a second sheet having at least a portion thereof formed of transparent synthetic resin film and including a proximate margin secured to said first sheet adjacent said opening, said second sheet also including a remote margin, a first side, a second side, and a pair of opposed edges defining therebetween a first transverse width;

a third sheet including a near margin secured to said first sheet adjacent to said opening and in opposition across said opening relative to said proximate margin of said second sheet, said third sheet further including a free margin, one side, another side, and a pair of opposed side edges presenting therebetween a second transverse width, said second sheet being configured for extension across said opening in overlying relationship to said body part, with said second side thereof in opposing relationship with the one side of said third sheet: and means for adhesively securing said second sheet to said body part, and for adhesively interconnecting respective portions of said second and third sheets.

18. The surgical drape of claim 17, said second sheet being formed entirely of transparent synthetic resin film.

19. The surgical drape of claim 17, said adhesive means including respective coatings of adhesive on said second side of said second sheet and said one side of said third sheet.

20. A surgical drape for facilitating surgery at a surgical site on a body part, said drape comprising:

a first base sheet presenting an upper surface, an opposed lower surface, an opening therethrough, and a surgical site region adjacent said opening, said opening being oriented for passage of a body part through the opening from said lower surface to said upper surface, with at least said surgical site of said body part over said surgical site region;

a second sheet presenting a top surface and an opposed bottom surface;

means operatively connecting said second sheet to said first sheet adjacent said opening, with said second sheet extending over said opening and said surgical site, said bottom surface of said second sheet being in face-to-face relationship with said upper surface of said first sheet; and means for adhering said second sheet to said body part portion.

21. The surgical drape of claim 20, including a third sheet presenting an upper surface and an opposed lower surface, said third sheet being secured to said first sheet adjacent said opening and extending over said region, said body part portion resting upon the upper surface of said third sheet and being disposed between said second and third sheets.

22. The surgical drape of claim 21, including means for interconnecting marginal portions of said second and third sheets.

23. The surgical drape of claim 20, at least the area of said second sheet disposed over said surgical site being transparent.

24. The surgical drape comprising:

a first base sheet presenting an upper surface, an opposed lower surface, and a body part-receiving opening therethrough;

a second sheet having one end margin thereof secured to said first sheet adjacent said opening and being of sufficient length and width when extended to cover said opening and a surgical site spaced from said opening, said second sheet being in a non-extended orientation with successive segments of the second sheet lying atop each other;

a third sheet having a first end margin thereof secured to said first sheet adjacent said opening and in generally opposed relationship to said one end margin of said second sheet across said opening, said third sheet being of sufficient length and width when extended to cover said surgical site beneath said second sheet, said third sheet being in a non-extended orientation with successive segments of the third sheet lying atop each other.

25. The surgical drape of claim 24, each of said first and second sheets being in a folded-together compact condition.

* * * * *